United States Patent [19]
Schiff et al.

[11] Patent Number: 5,951,465
[45] Date of Patent: Sep. 14, 1999

[54] DEVICE FOR CARRYING OUT MANIPULATIONS IN THE HUMAN BODY

[75] Inventors: Norman Schiff, Meersburg; Horst Dittrich, Immendingen, both of Germany

[73] Assignee: Karl Storz GmbH & Co., Germany

[21] Appl. No.: 09/068,904

[22] PCT Filed: Nov. 22, 1996

[86] PCT No.: PCT/DE96/02251

§ 371 Date: Aug. 3, 1998

§ 102(e) Date: Aug. 3, 1998

[87] PCT Pub. No.: WO97/18757

PCT Pub. Date: May 29, 1997

[30] Foreign Application Priority Data

Nov. 22, 1995 [DE] Germany ............ 195 43 576

[51] Int. Cl.[6] .................................................. A61B 17/00
[52] U.S. Cl. ...................... 600/224; 600/235; 600/245; 606/119
[58] Field of Search .................... 600/184, 201, 600/204, 214, 217, 219, 224, 235, 245; 606/119

[56] References Cited

U.S. PATENT DOCUMENTS

| | | | |
|---|---|---|---|
| 4,633,869 | 1/1987 | Schmieding . | |
| 5,199,419 | 4/1993 | Remiszewski et al. | 600/204 |
| 5,235,966 | 8/1993 | Jamner | 600/214 X |
| 5,271,385 | 12/1993 | Bailey | 600/214 |
| 5,353,784 | 10/1994 | Nady-Mohamed | 606/119 X |
| 5,522,839 | 6/1996 | Pilling | 600/204 X |

FOREIGN PATENT DOCUMENTS

| | | | |
|---|---|---|---|
| 94/21179 | 9/1994 | WIPO | 600/204 |
| WO 94/29934 | 9/1994 | WIPO . | |

*Primary Examiner*—Jeffrey A. Smith
*Attorney, Agent, or Firm*—St.Onge Steward Johnston & Reens LLC

[57] ABSTRACT

Disclosed is a device for carrying out manipulations in the human body, in particular in the uterus. The device includes a hook element provided with at least one hook which is connected via a rod, which is guided in a shaft, to a grip end provided at a proximal end of the device in such a manner that the hook can be pivoted in and out. The invention is distinguished by a glide element which is guided in a sliding manner on the shaft in the longitudinal direction thereof and is provided at its distal end with an approximately bell-shaped expansion.

7 Claims, 2 Drawing Sheets

The present invention is made more apparent in the
DEVICE FOR CARRYING OUT MANIPULATIONS IN THE HUMAN BODY

DESCRIPTION

1. Technical field

The present invention relates to a device for carrying out manipulations in the human body, in particular in the uterus.

2. State of the Art

Devices according to the generic part of claim 1 are, by way of illustration, manufactured and sold by Karl Storz GmbH & Co. These known devices have a hook element, the hook of which is connected to grip ends provided at the proximal end of the device via a rod, which is guided in a shaft.

By expanding and contracting the hooks, manipulations can be carried out in the human body, in particular in the uterus.

The known devices or instruments have the drawback that in some applications it is difficult to carry out the desired manipulation, because the tissue sections to be manipulated with the hook(s) give way sideways.

DESCRIPTION OF THE INVENTION

The object of the present invention is to further improve a generic device for carrying out manipulations in the human body, in particular in the uterus, in such a manner that the desired manipulation can be carried out in instances in which the to-be-manipulated tissue sections give way sideways.

An invented solution to this object is disclosed.

An element of the present invention is to provide a glide element guided in a sliding manner on a shaft in the longitudinal direction thereof and at the distal end of which an approximately bell-shaped expansion is provided. By sliding this glide element, the to-be manipulated tissue sections can be manipulated together with the clapped open hook(s). In particular, with the glide element, the tissue can be "gripped" by interacting with the hook(s).

Further embodiments of the present invention are the subject matter of the disclosure.

It is particularly preferred if the glide element is provided with an illumination device with a light exit at the peripheral edge of the bell-shaped expansion, thereby permitting illuminating the to-be-manipulated section of tissue, if need be, in addition to an endoscope illumination. In particular, however, the position of the edge of the bell can be determined laparoscopically.

In one aspect of the invention, the expansion has approximately the shape of a hemisphere, has the advantage that the expansion cannot get caught in the tissue or in the corporal opening when removed or withdrawn.

Further disclosed is an especially ergonomically advantageous embodiment in which a drive unit is provided for the glide element which is provided with a hand wheel which moves a ball guided in a longitudinal groove over a screwthread-shaped groove. Thus, in order to move the glide element in a longitudinal direction, the operating person only has to turn his/her hand.

The hook element may be provided in an as such known manner with at least three, preferably four, hooks which, when the grip ends are open, are clapped shut and which are clapped open in the direction toward the distal end by closing the grips ends by the rod acting like a drawrod.

Further embodiments simplify cleaning and sterilizing the invented device. In particular, the hook element, the shaft and the grip may be connected in a known manner, such as described in EP-A-0 688 187.

BRIEF DESCRIPTION OF THE DRAWING

The present invention is made more apparent in the following using the accompanying drawing, in which.

DESCRIPTION OF A PREFERRED EMBODIMENT

Figure 1:
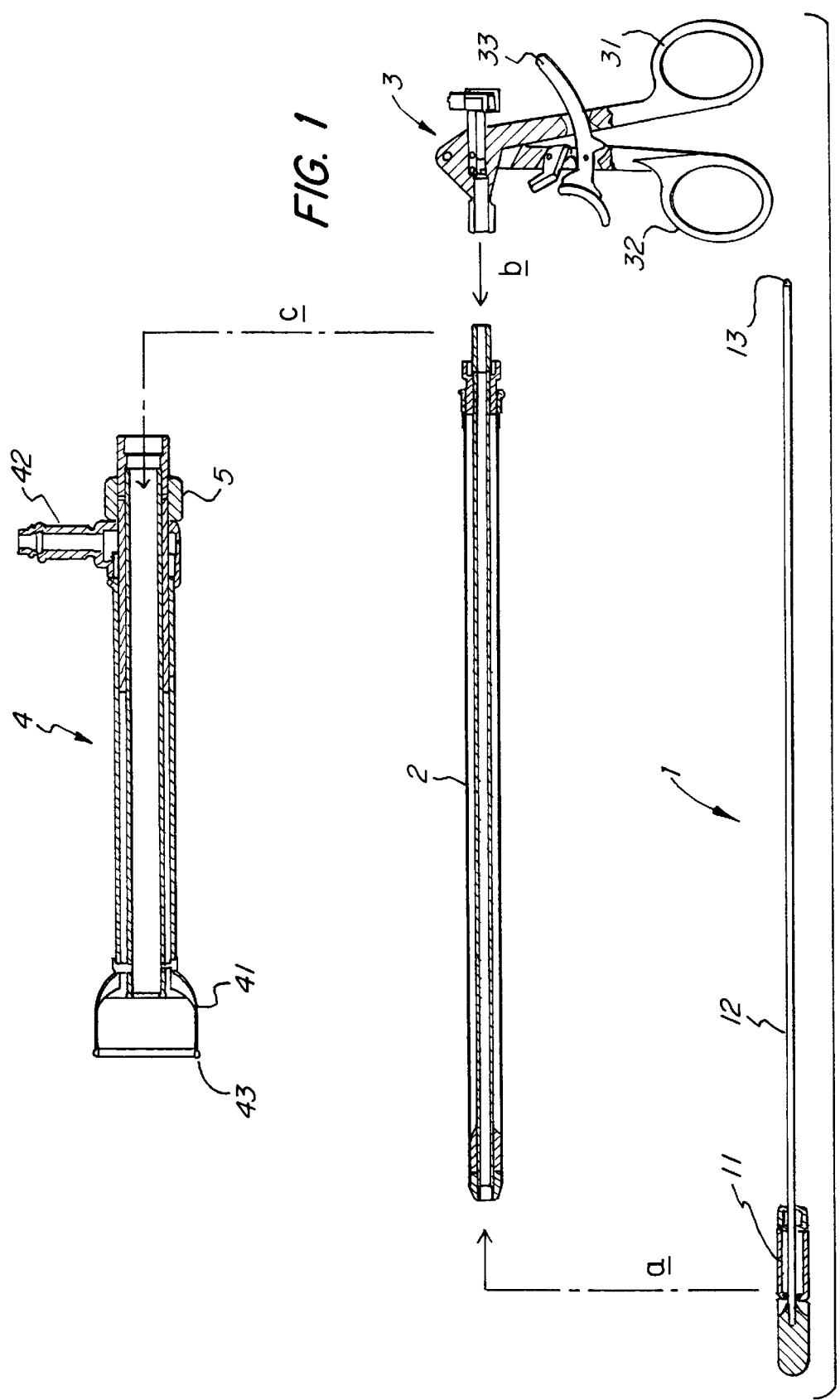
FIG. 1 shows a detailed representation of a uterus manipulator designed according to the present invention.

FIG. 1 shows the essential components of an invented device for carrying out manipulations in the human body, which particularly functions as a uterus manipulator. The device is provided with a hook unit 1, which bears at its distal end a hook element 11, which will be described in more detail in the following paragraphs. Hook element 11 is connected via an (actuating) rod 12 to the proximal end of the uterus manipulator. Provided at the proximal end of rod 12 is a ball 13, the function of which will be described in the following paragraphs. Hook unit 1 is inserted into a shaft 2 of the device as is indicated by arrow a. The connection between hook unit 1 and shaft 2 is a bayonet connection. At the proximal end, spring hemispheres, such as described by way of illustration in EP-A-0 688 187, are provided as locking means.

Connected to the proximal end of shaft 2 is a grip end 3 having grips 31 and 32 and a locking piece 33, by way of illustration by means of a screw connection, but also by means of any other suited connection (see arrow b). Grips 31 and 32 can be fixed in a specific position by means of locking piece 33. Ball 13 is connected by means of a lockable ball connection to the moveable grip 32 of grip end 3.

As described in the preceding, the instrument is essentially known from the so-called Take-apart Tongs of Karl Storz GmbH & Co. or from the mentioned EP-A-0 688 187 thereby obviating a more detailed description and instead reference is made to the cited state of the art.

An element of the present invention is that a glide element 4 is provided which is provided at its distal end with a bell-shaped expansion 41. A connection piece 42 for connecting an illumination device is provided in the proximal region of glide element 4. The light emitted by the illumination device is led by means of light guides (known in endoscopy) to the distal end. The light exit is provided in the peripheral edge 43 of expansion 41.

Glide element 4 is placed on shaft 2 (arrow c) before the connection of hook unit 1 to the shaft 2. Then grip end 3 is connected to external shaft 2 and to the proximal end of rod 12.

Figure 2:
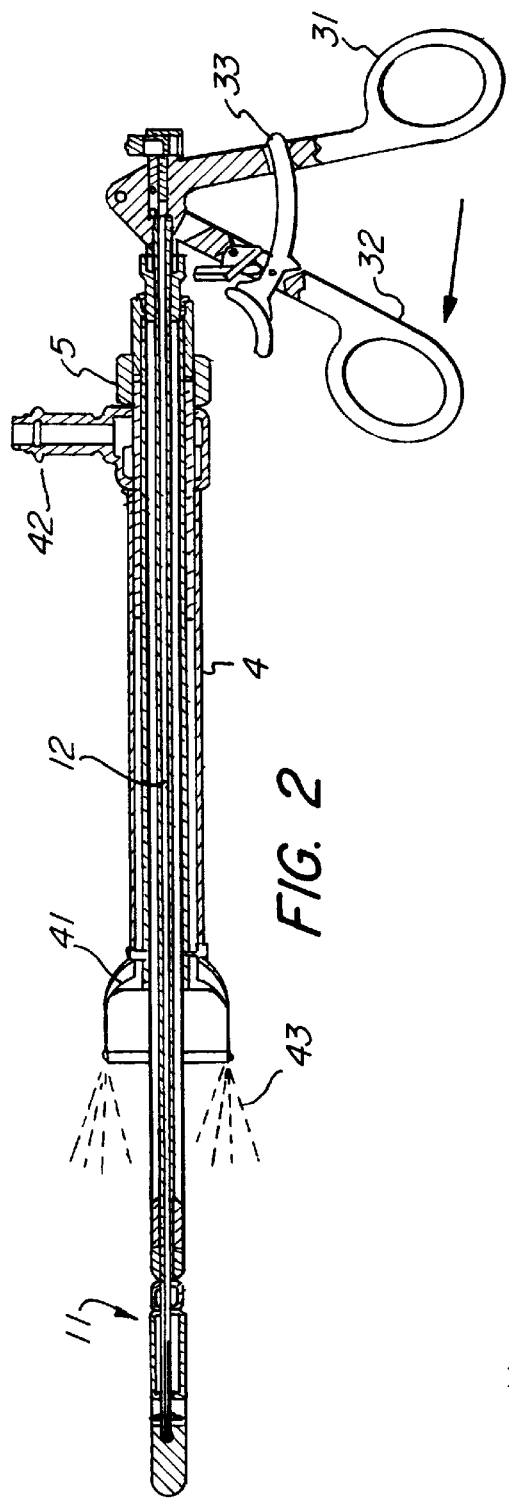
FIG. 2 shows the assembled uterus manipulator with a closed hook element.
Figure 3A:
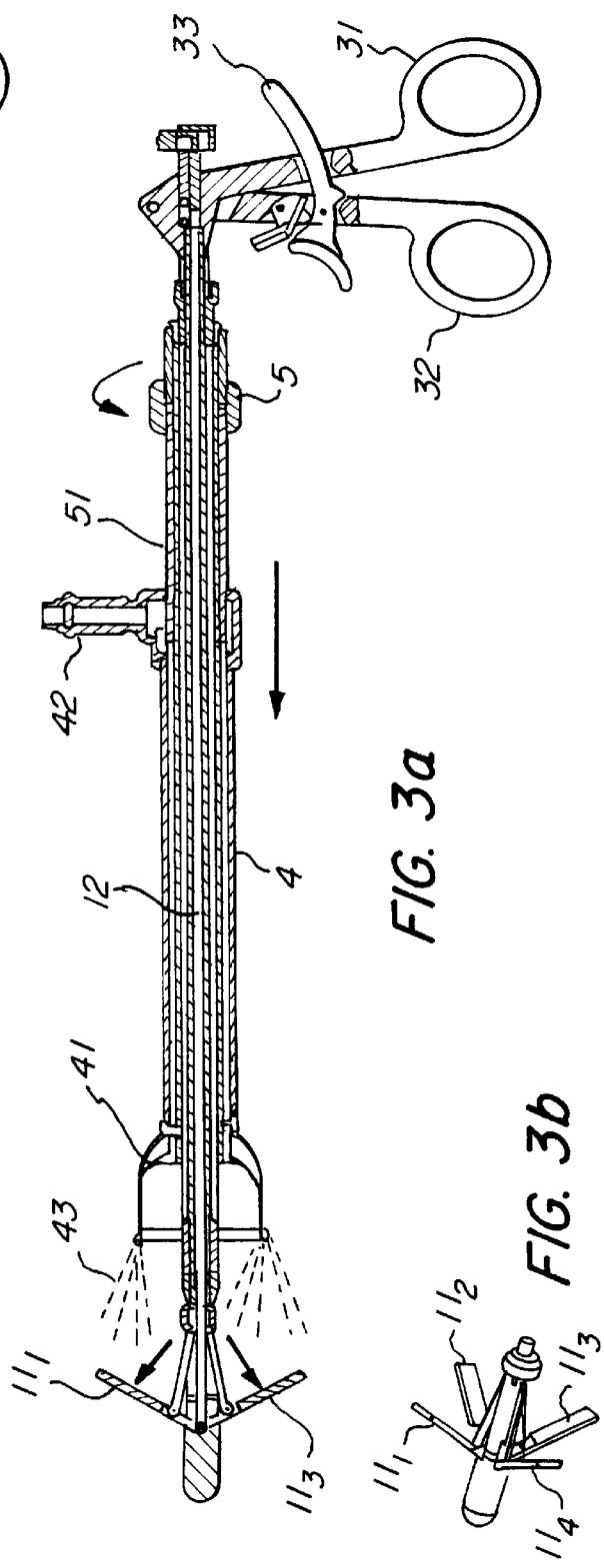
FIG. 3a shows the uterus manipulator depicted in FIG. 2 with an open hook element.
Figure 3B:
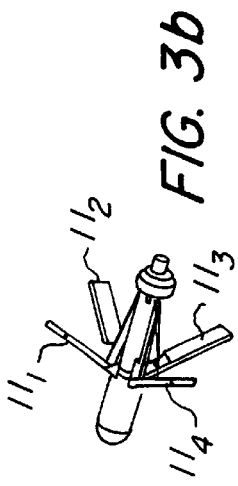
FIG. 3b shows an exploded view of the hook element with four hooks.

FIGS. 2 and 3 show the assembled uterus manipulator designed according to the present invention:

The hook element 11 which, as FIG. 3b shows, is provided with four 11$_1$ to 11$_4$ hooks, is designed in such a manner that the hooks are clapped shut when grips 31 and 32 are open. By closing respectively pressing together the grip ends, the hooks are clapped open in the direction of the distal end by rod 12 acting as a drawrod. In order to carry out the desired manipulations, glide element 4 is moved by turning a hand wheel 5 in the direction of the longitudinal axis of shaft 2. For this purpose a ball 51 is provided which is led in a longitudinal groove and which is moved over a screwthread-shaped groove in the direction of the longitudinal axis of the instrument respectively of the manipulator.

The manipulation carried out with hooks $11_1$ to $11_4$ can be supported by drawing glide element 4 to and fro. In addition, illumination light emerges from the peripheral edge of bell-shaped expansion 41 in order to be able to determine laparoscopically the position of the edge of the bell of the vaginally inserted instrument.

In the preceding, the present invention has been described without the intention of limiting the spirit or scope of the overall inventive idea, within which, of course, a variety of modifications are possible: the basic instrument can be constructed in a different manner than the described preferred embodiment. The thrust of the glide element may also occur in a different manner than the described one.

What is claimed is:

1. A device for carrying out manipulations in the human body having a rod guided in a shaft, a grip mounted to a proximal end of the shaft for actuating said rod, a hook element provided with at least one hook, said hook element connected via said rod to said grip in such a manner that said at least one hook can be pivoted in and out, and a glide element guided in a sliding manner on said shaft in a longitudinal direction thereof and provided at a distal end with an approximately bell-shaped expansion, said glide element provided with an illumination device having a light exit provided in said expansion.

2. A device according to claim 1, characterized by the fact that an illumination device the light exit of which is provided in the peripheral edge of said expansion.

3. A device according to claim 1, characterized by the fact that said glide element is provided with a hand wheel which moves a ball in a longitudinal groove over a screwthread-shaped groove.

4. A device according to claim 3, characterized by the fact that said hook element, said shaft and said grip can be separated from each other.

5. A device according to claim 4, characterized by the fact that said hook element, said hand wheel, said shaft and said grip can be separated from each other.

6. A device according to claim 1, characterized by the fact that said hook element is provided with at least three, preferably four, hooks which are clapped shut when said grip ends are open and which are clapped open by closing said grip ends.

7. A device according to claim 1, characterized by the fact that said rod is connected to said grip in a detachable manner.

* * * * *